US00PP25313P3

(12) United States Plant Patent
Heuger

(10) Patent No.: US PP25,313 P3
(45) Date of Patent: Feb. 24, 2015

(54) ***HELLEBORUS* PLANT NAMED 'COSEH 980'**

(50) Latin Name: ***Helleborus niger*×*Helleborus*×*sternii***
Varietal Denomination: COSEH 980

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 126 days.

(21) Appl. No.: 13/815,554

(22) Filed: Mar. 8, 2013

(65) Prior Publication Data

US 2014/0150153 P1 May 29, 2014

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 980', characterized by its upright and mounding plant habit; uniform and freely flowering habit; dark green-colored leaves; freely flowering habit; single white and yellow green-colored flowers; and good garden performance.

2 Drawing Sheets

Botanical designation: *Helleborus niger*×*Helleborus*×*sternii*.

Cultivar denomination: 'COSEH 980'.

BACKGROUND OF THE INVENTION

The present invention relates to a new and distinct cultivar of *Helleborus* plant, botanically known as *Helleborus niger*×*Helleborus*×*sternii* and hereinafter referred to by the name 'COSEH 980'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2007 of an unnamed proprietary seedling selection of *Helleborus niger*, not patented, as the female, or seed, parent with an unnamed proprietary seedling selection of *Helleborus*×*sternii*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2009.

Asexual reproduction of the new *Helleborus* plant by divisions in a controlled greenhouse environment in Glandorf, Germany since March, 2009 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 980'. These characteristics in combination distinguish 'COSEH 980' as a new and distinct *Helleborus* plant:

1. Upright and mounding plant habit.
2. Uniform and freely flowering habit.
3. Dark green-colored leaves.
4. Freely flowering habit.
5. Single white and yellow green-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus lividus* 'COSEH 710', disclosed in U.S. Plant Pat. No. 21,063. In side-by-side comparisons conducted in Glandorf, Germany, plants of the new *Helleborus* differed primarily from plants of 'COSEH 710' in sepal color as plants of 'COSEH 710' had light green-colored sepals tinged with reddish pink overtones.

Plants of the new *Helleborus* can also be compared to plants of *Helleborus niger*×*Helleborus lividus* 'COSEH 700', disclosed in U.S. Plant Pat. No. 21,003. In side-by-side comparisons conducted in Glandorf, Germany, plants of the new *Helleborus* differed primarily from plants of 'COSEH 700' in sepal color as plants of 'COSEH 700' had light green-colored sepals tinged with greyed purple.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 980' grown in a container.

The photograph on the second sheet is a close-up view of a typical flower of 'COSEH 980'.

DETAILED BOTANICAL DESCRIPTION

The aforementioned photographs and following observations, measurements and values describe plants grown during the late autumn in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus*×*sternii* 'COSEH 980'.

Parentage:

*Female, or seed, parent.*—Unnamed proprietary seedling selection of *Helleborus niger*, not patented.

*Male, or pollen, parent.*—Unnamed proprietary seedling selection of *Helleborus*×*sternii*, not patented.

Propagation:

*Type.*—By tissue culture.

*Time to initiate roots, winter.*—About two months at temperatures about 12° C.

*Time to produce a rooted young plant, winter.*—About six months at temperatures about 4° C. to 15° C.

*Root description.*—Thick to thin, fleshy; white to brown in color.

*Rooting habit.*—Sparse.

Plant description:

*Plant and growth habit.*—Herbaceous perennial; upright and mounding plant habit with flowers held just above the foliar plane; plant shape is roughly ovate; moderately vigorous growth habit.

*Plant height.*—About 22.5 cm.

*Plant diameter* (*area of spread*).—About 42.3 cm.

Foliage description:

*Arrangement.*—Leaves arranged in a basal rosette; leaves palmately compound with five leaflets per leaf.

*Leaf length.*—About 15.2 cm.

*Leaf width.*—About 18.1 cm.

*Leaflet length.*—About 11.4 cm.

*Leaflet width.*—About 4.1 cm.

*Leaf shape.*—Palmate; orbicular to reniform in outline.

*Leaflet shape.*—Ovate to narrowly elliptic.

*Leaflet apex.*—Acute.

*Leaflet base.*—Cuneate.

*Leaflet margin.*—Serrate.

*Leaflet texture, upper and lower surfaces.*—Smooth, glabrous; leathery.

*Leaflet venation pattern.*—Pinnate.

*Leaflet color.*—Developing leaves, upper surface: Close to 137A. Developing leaves, lower surface: Close to 148A. Fully developed leaves, upper surface: Between N137A and 147A; venation, close to 144C, at the base, tinged with close to 200B. Fully developed leaves, lower surface: Close to 147B; venation, close to N199B.

*Petioles.*—Length: About 10.5 cm. Diameter: About 7 mm. Texture, upper and lower surfaces: Smooth, glabrous. Color, upper and lower surfaces: Close to 146D heavily dotted with close to N199B and close to 200A at the base.

Flower description:

*Flower shape and habit.*—Single rotate flowers arranged in panicles; freely and uniform flowering habit with about 14 flowers per panicle and about 60 flowers and flower buds developing per plant; flowers facing outwardly to slightly upright and nodding.

*Fragrance.*—None detected.

*Natural flowering season.*—Plants begin flowering about ten months after planting; plants flower from late autumn into the winter in Germany.

*Flower longevity on the plant.*—About ten days; flowers not persistent.

*Flower buds.*—Length: About 1.6 cm. Diameter: About 1.1 cm. Shape: Ovate. Color: Close to 145C flushed with close to 174D.

*Inflorescence height* (*including peduncle*).—About 19.7 cm.

*Inflorescence diameter.*—About 15 cm.

*Flower diameter.*—About 7.6 cm.

*Flower depth* (*height*).—About 2.4 cm.

*Petals.*—Transformed into nectaries.

*Sepals.*—Quantity and arrangement: Five, arranged in a single whorl. Length: About 4 cm. Width: About 3.9 cm. Shape: Broadly ovate to orbicular. Apex: Rounded. Base: Broadly cuneate. Margin: Entire. Texture, upper and lower surfaces: Smooth, glabrous. Color: When opening, upper surface: Close to between 155A and 150D; towards the base, close to 145B to 145C. When opening, lower surface: Close to between 155A and 150D; towards the base, tinged with close to 182D. Fully opened, upper surface: Close to between 145C to 145D and 150D; towards the base, close to 145B; with development, color becoming closer to 146D. Fully opened, lower surface: Close to 145C to 145D; central band, close to 177C.

*Peduncles.*—Length: About 11.8 cm. Diameter: About 9 mm. Aspect: About 10° from vertical. Strength: Strong. Texture: Smooth, glabrous. Color: Close to 145D, heavily dotted with close to 177A.

*Pedicels.*—Length: About 3.8 cm. Diameter: About 4 mm. Aspect: About 20° from peduncle axis. Strength: Moderately strong. Texture: Smooth, glabrous. Color: Close to 145D, heavily dotted with close to 177A.

*Reproductive organs.*—Stamens: Quantity per flower: About 100. Filament length: About 1.7 cm. Filament color: Close to NN155D. Anther shape: Reniform. Anther length: About 2 mm. Anther color: Close to 154C. Pollen amount: Scarce. Pollen color: Close to 4C. Pistils: Quantity per flower: About six. Pistil length: About 1 cm. Stigma shape: Club-shaped. Stigma color: Close to 154D. Style length: About 9 mm. Style color: Close to 157D. Ovary color: Close to 150D. Nectaries (transformed petals): Quantity per flower: About 14. Length: About 1.3 cm. Diameter: About 4 mm. Shape: Narrowly triangular, flattened tubular. Color, immature, inner and outer surfaces: Close to 144A to 144B. Color, mature, inner and outer surfaces: Close to N144A; towards the apex, close to 151B; with development, color becoming closer to 151A.

*Seeds and fruits.*—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 980' as illustrated and described.

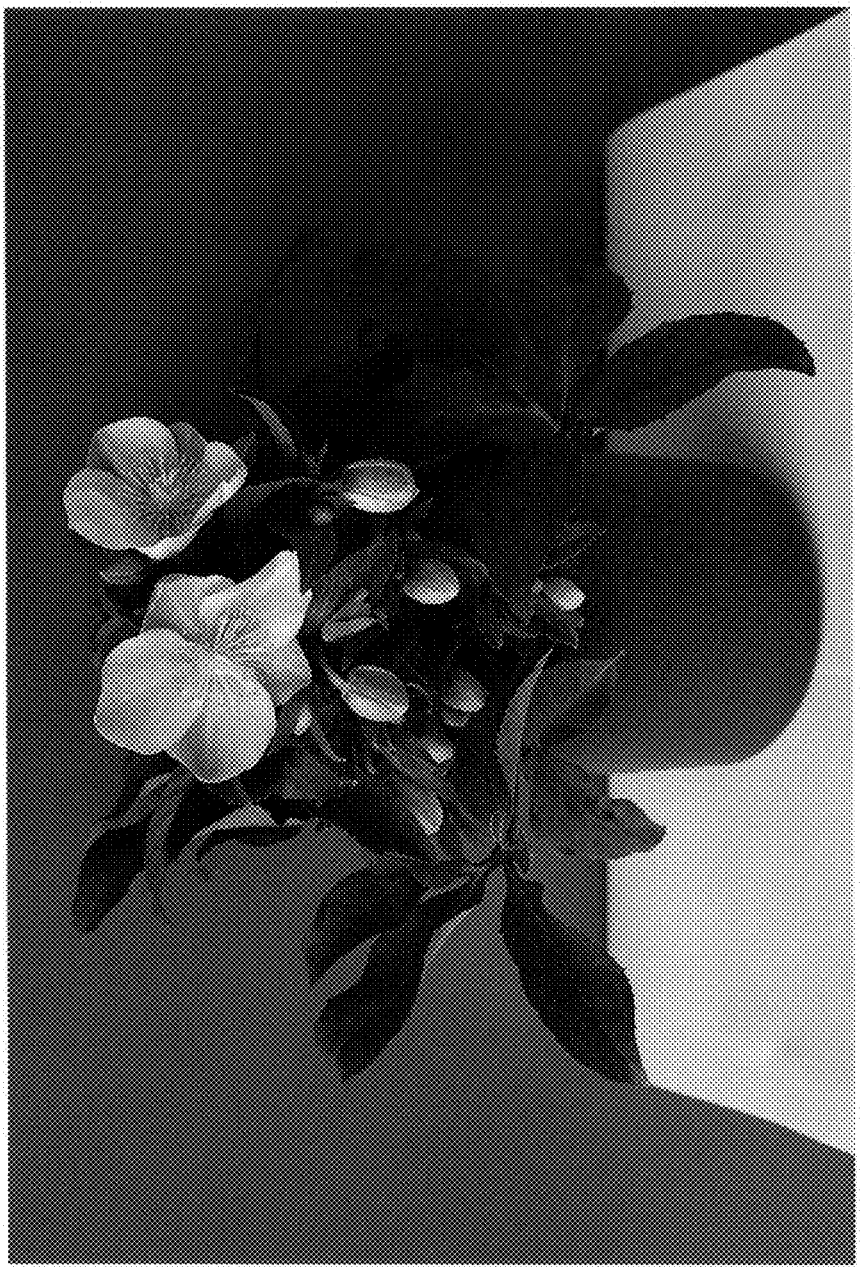

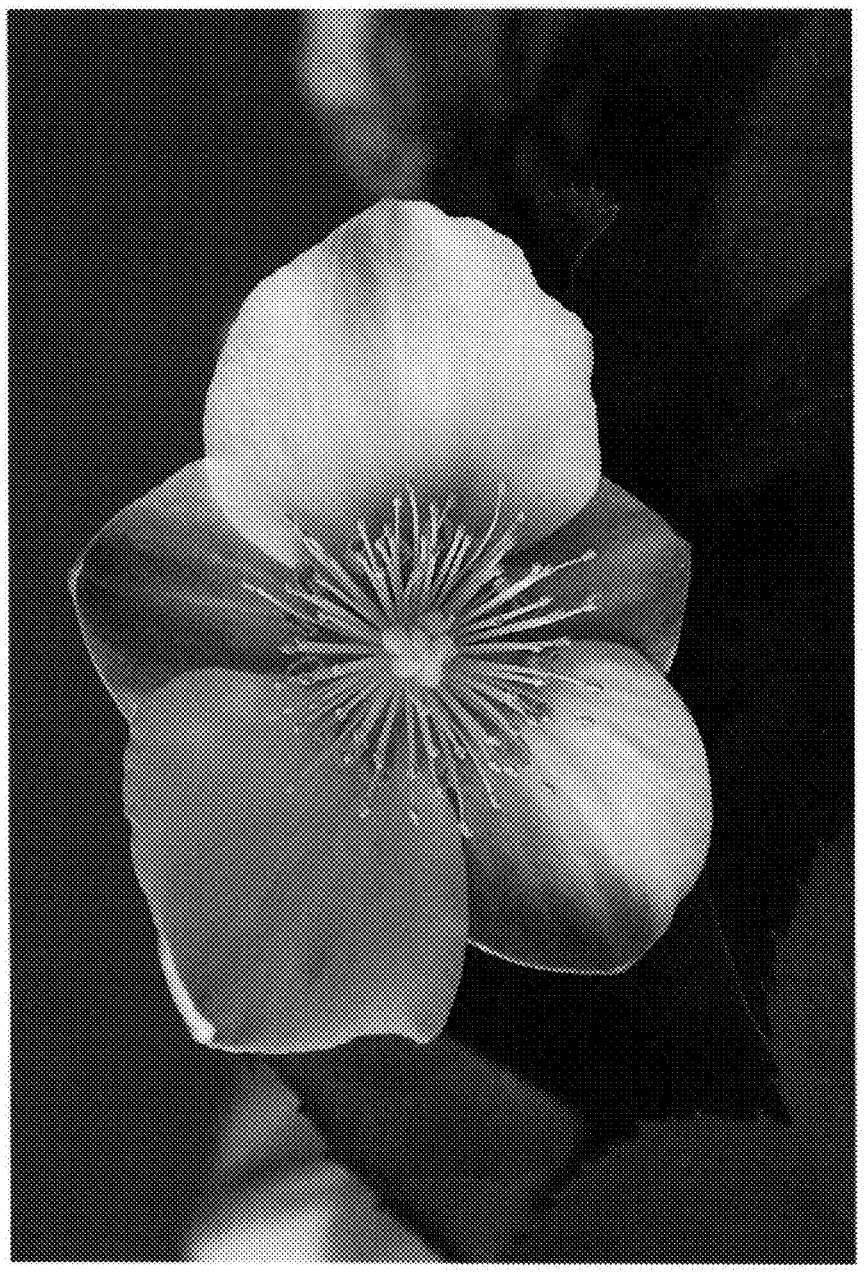

* * * * *